United States Patent
Diehl et al.

(10) Patent No.: US 7,780,829 B2
(45) Date of Patent: Aug. 24, 2010

(54) SENSOR ELEMENT AND METHOD FOR DETERMINING THE CONCENTRATION OF GAS COMPONENTS IN A GAS MIXTURE

(75) Inventors: Lothar Diehl, Gerlingen (DE); Marcus Scheffel, Erlangen (DE)

(73) Assignee: Robert Bosch GmbH, Stuttgart (DE)

( * ) Notice: Subject to any disclaimer, the term of this patent is extended or adjusted under 35 U.S.C. 154(b) by 888 days.

(21) Appl. No.: 11/632,833

(22) PCT Filed: Aug. 18, 2005

(86) PCT No.: PCT/EP2005/054078
§ 371 (c)(1),
(2), (4) Date: Jan. 19, 2007

(87) PCT Pub. No.: WO2006/037689
PCT Pub. Date: Apr. 13, 2006

(65) Prior Publication Data
US 2008/0245666 A1  Oct. 9, 2008

(30) Foreign Application Priority Data
Oct. 5, 2004 (DE) .................. 10 2004 048 318

(51) Int. Cl.
*G01N 27/409* (2006.01)
*G01N 27/41* (2006.01)
(52) U.S. Cl. .................. 204/429; 204/406; 205/781; 205/783.5; 205/784.5
(58) Field of Classification Search ......... 204/421–429; 205/781, 783.5, 784.5; 73/114.71–114.73
See application file for complete search history.

(56) References Cited

U.S. PATENT DOCUMENTS

| 5,391,284 A  * | 2/1995 | Hotzel .................. 204/425 |
| 6,332,966 B1 * | 12/2001 | Sakai et al. .............. 204/425 |
| 2005/0252771 A1* | 11/2005 | Wiedenmann et al. ...... 204/426 |

FOREIGN PATENT DOCUMENTS

| DE | 199 41 051 A1 | 3/2001 |
| DE | 100 31 474 A1 | 4/2001 |
| DE | 102 16 724 C1 | 10/2003 |

* cited by examiner

*Primary Examiner*—Nam X Nguyen
*Assistant Examiner*—Kourtney R Salzman
(74) *Attorney, Agent, or Firm*—Merchant & Gould P.C.

(57) ABSTRACT

A sensor element for the determination of the concentration of gas components in a gas mixture, particularly of the concentration of gas components in the exhaust of internal combustion engines, with two electrodes, that together with a solid electrolyte constitute a pumping cell, whose outer pumping electrode is exposed to the gas mixture by way of a porous protective layer, and with a reference electrode, which is disposed on the solid electrolyte and is exposed to a reference gas, and which with a solid electrolyte and a Nernst electrode constitutes a concentration or Nernst cell, is thereby characterized in that at least periodically the Nernst voltage between the outer pumping electrode and the Nernst electrode is tapped and analyzed.

6 Claims, 1 Drawing Sheet

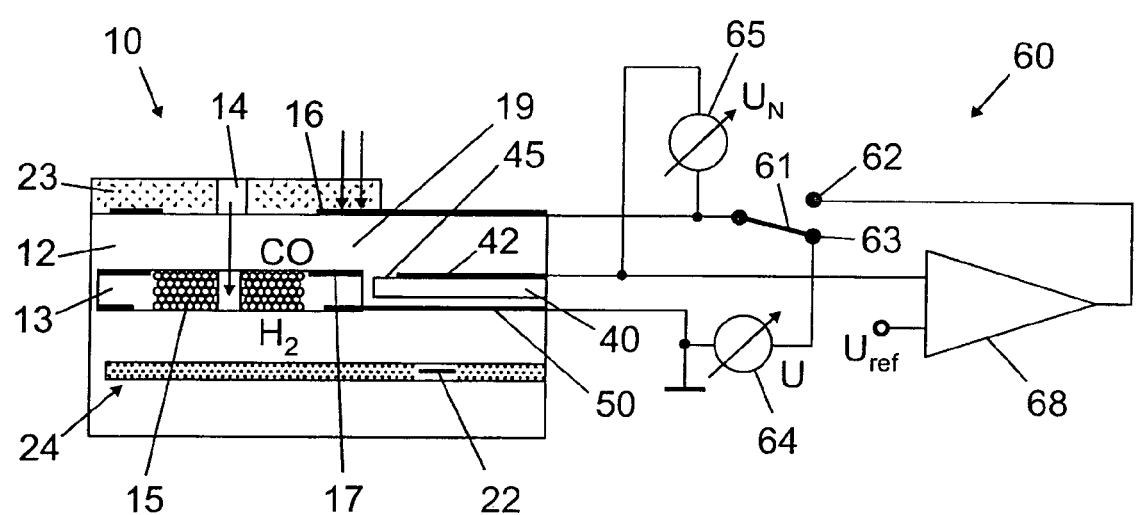

SENSOR ELEMENT AND METHOD FOR DETERMINING THE CONCENTRATION OF GAS COMPONENTS IN A GAS MIXTURE

The invention concerns a sensor element for determining a concentration of gas components in a gas mix, particularly the concentration of gas components in the exhaust gas of internal combustion engines, as well as a procedure for operation of such a sensor element according to the genus of the independent claims 1 and 4.

A sensor element according to the class for a wideband lambda sensor is known from the German patent DE 199 41 051 A1. This sensor element has a sensor body consisting of solid electrolyte layers, in which a cavity or measuring space connected with the exhaust gas via a diffusion barrier, and a reference gas duct, which has been loaded by a reference gas, are designed. A pumping cell to pump the oxygen into the cavity (rich exhaust gas) or out of the measurement space (lean exhaust gas) is comprised of an outer pumping electrode, which is disposed on the solid electrolyte body and covered by a porous protective layer, and an inner pumping electrode disposed in the cavity. The porous protective layer covering the outer pumping electrode has a larger limit current than does the diffusion barrier. A concentration—or Nernst cell includes a measurement—or Nernst electrode disposed in the measuring space and a reference electrode disposed in the reference gas duct. The limit current flowing between the pumping electrodes during adjustment of a constant voltage of, for example, 450 mV between the Nernst and reference electrode, is at constant total pressure a measurement for the lambda value of the exhaust gas. The sensitivity of the sensor element is adjusted by way of the limit current designated through the diffusion barrier.

As the partial pressure which determines the limit current is proportional to total pressure and mole fraction, such a sensor element displays a dynamic pressure dependence, which manifests itself in such a manner, that pressure peaks in the exhaust gas appear as an output signal of the Lambda sensor, although these are not connected causally with the change of the gas composition. The sensitivity to total pressure changes at low frequencies by way of the diffusion barrier. The diffusion barrier is, however, not supposed to reduce the sensitivity to mole fraction changes, the knowledge of which is required for the adjustment of the optimal exhaust gas composition for the combustion in the engine.

As a result of the diverse molecule masses, different types of gas have, therefore, different thermal velocities and for this reason diverse diffusion coefficients. On this account the sensitivity of the sensor is dependent upon the type of gas. As the sensor delivers only one total current as an output signal, a concentration change for an individual gas component can no longer be clearly distinguished from the change in the type of gas.

Therefore, the task underlying the invention is to bring about in a technically simple way a sensor element capable of being implemented for the determination of the concentration of a gas component in a gas mix and a procedure to operate such a sensor element, whereby an individual gas component can be distinguished from a change in the type of gas.

The task is solved by means of the characteristics of the claims 1 and 4. Advantageous further configurations and embodiments of the sensor element and the procedure to operate such a sensor element are the subject matter of the sub-claims that refer back to the independent claims.

It is the basic idea of the invention, to operate a previously described wideband sensor in the dispersion operation as a Nernst cell with two protective layers differing in thickness. In so doing, due to the different diffusion coefficients of gas mixtures, which are not in balance, and which are abreacting at the electrode, a Nernst voltage arises between the two electrodes. Thereby, the negative pole of the Nernst voltage, for example, arises at the electrode behind the thicker of the two protective layers, if the oxygen depleted gas diffuses more quickly. For at least a periodic tap of the Nernst voltage (dispersion differential voltage) changes are in an especially advantageous manner not required at the sensor element itself. Only the circuit of the sensor element has to be changed.

Through admission of the sensor with a total pressure increase (pressure pulsation), the dynamic viscosities of the gas components break down in the chronological progression of the dispersion signal and can be analyzed.

By employing the catalytic converter down stream, a detection, whether the reactions of the combustion process have taken place or not, is thereby possible. As, for example, in the case of oxygen, as soon as all reactions have taken place, the identical partial pressures behind both of the protective layers appear (that is to say behind the protective layer of the outer pumping electrode and of the diffusion barrier). In this manner, the amount of aging of the catalytic converter can also be determined. Thus, an aging must be assumed, if the identical partial pressure does not appear.

In a particularly advantageous manner, both Nernst voltages can thereby be measured in comparison to the reference electrode; and in so doing, the absolute Nernst voltage can be determined as by a conventional Lambda=1–jump sensor. This signal allows itself to be used for the regulation of the combustion process in the vicinity of Lambda=1.

The Nernst voltage is preferably in this instance tapped between the reference electrode and the outer pumping electrode. In so doing, the voltage at the outer pumping electrode is measured without pumping current.

An especially advantageous form of embodiment makes provision for a medium to commutate the pumping voltage between a switching unit, through which the pumping voltage is controlled by a set point as a function of the deviation of the output voltage of the Nernst cell between the measuring gas space and a reference gas volume, which corresponds to the "normal operation" of this sensor, and a tap of the voltage between the outer pumping electrode and a inner pumping electrode, which corresponds to the "dispersion operation" of this sensor. This commutating medium allows accordingly in a simple manner for the commutation between the operation of the switching unit for the generation of a functional pumping current and the voltage metering.

DRAWING

Further advantages and characteristics of the invention are subsequently explained on the basis of an embodiment example of the invention.

The FIGURE shows a sensor element according to the invention for the determination of the concentration of a gas component in a gas mixture.

The sensor element, which is schematically depicted for the determination of the concentration of gas components in a gas mixture, particularly the concentration of gas components in the exhaust gas of internal combustion engines, has a planar sensor body 10, which is exposed to the exhaust gas of the (not depicted) internal combustion engine, respectively another gas mixture. The sensor body 10 is itself comprised of a solid electrolyte 12, for example a $ZrO_2$ ceramic stabilized with $Y_2O_3$, in which, for example, a ring shaped cavity 13 is designed. The cavity 13 is located above a central opening 14, which is positioned vertically into a solid electrolyte 12, and is in connection with the exhaust gas and is covered vis-à-vis the opening 14 by a porous diffusion barrier 15. On the top side of the solid electrolyte 12, an extensive outer pumping electrode 16 covered by a porous protective layer 23 is disposed and an inner pumping electrode 17 is disposed inside the cavity 13 on the side of the solid electrolyte 12 which faces opposite to the outer electrode 16. The inner pumping electrode 17 is designed annularly shaped in the embodiment example and set to a zero voltage potential.

A voltage U, which will subsequently be addressed in more detail, lies at the outer pumping electrode 16 which is likewise annularly shaped and encompasses the central opening 14.

The outer pumping electrode 16 and the inner pumping electrode 17 constitute together with the solid electrolyte 12 a pumping cell 19.

A reference gas volume 40 is disposed essentially in the same plane as the cavity 13. A reference electrode 42 is superimposed on a solid electrolyte 12 within the reference gas volume 40. A Nernst electrode 50 lies opposite to the inner pumping electrode 17 in the area of the cavity 13, which is also denoted as a gas measurement space, and it (the Nernst electrode) like the inner pumping electrode is designed annularly shaped. The Nernst electrode 50 lies at a zero voltage potential just like the inner pumping electrode.

The inner pumping electrode 17 and the reference electrode 42 disposed in the reference gas volume 40 constitute together a Nernst, respectively a concentration cell 45.

A heater 22, which, for example, can be designed meander shaped, is disposed beneath the cavity 13 and the reference gas volume 40. The heater 22 heats the solid electrolyte 12 to a specified temperature required for the measurement. For this purpose provision is made for a known control circuit, which is not depicted in the figure.

The sensor element is activated in the subsequently described manner by means of an activation electronic circuit denoted in its entirety with a reference sign 60. The activation electronic circuit 60 comprises a commutation medium 61, through which commutation takes place between a switching position 62, in which the sensor element is operated in an inherently known manner, and a further switching position 63, which is addressed in more detail further down.

Provision is made for an operational amplifier 68, at whose input a reference voltage $U_{ref}$ lies, and on whose other input the voltage lying at the reference electrode 42 lies, which is in the one switching position 62 of the commutating medium 61. At a Nernst voltage $U_N$ smaller than, for example, 450 mV, the output of the operational amplifier 68 will be positive and drives a positive current through the pumping cell 19, or expressed in another way: a comparatively small Nernst voltage $U_N$, which corresponds to an oxygen surplus in the gas measuring space 13, leads to a transport (of negative) oxygen ions from the gas measurement space 13 to the exhaust gas. A comparatively high Nernst voltage $U_N$ leads accordingly to an oxygen rich stream of the exhaust gas to the gas measurement space 13, so that in a steady state a specified concentration of oxygen appears in the gas measurement space 13. The output of the operational amplifier 68 lies in such a state as a pumping voltage U in an inherently known manner at the outer pumping electrode 16.

In its second switching position, the commutating medium 61 connects a voltage meter (volt meter) 64 with the outer pumping electrode 16. In this switching position the dispersion differential voltage, the voltage between the Nernst electrode 50 and the outer pumping electrode 16, is tapped. Concurrently in this switching position of the commutating medium 61, the Nernst voltage between the outer pumping electrode 16 and the reference electrode 42 can be measured by means of the voltage meter 65, and, thus, the absolute Nernst voltage $U_N$ can be determined as with a conventional Lambda=1–jump sensor.

A detection whether the exhaust gas has been "fully cured" or not is possible in this way, when the sensor element is employed down stream of the catalytic converter of the internal combustion engine. That means in fact to see, whether the exhaust gas has gas components, which were subject to a chemical reaction during the combustion process. In these instances, unequal partial pressures will appear behind both of the protective layers, i.e. respectively behind the protective layer 23 and the porous diffusion barrier 15. From this conclusions can also be drawn about the aging of the catalytic converter.

Furthermore, due to the chronological progression of the measuring signal during pressure pulsations, conclusions can be drawn about the viscosity of the gas components.

Instead of a previously described dispersion voltage measurement, a measurement of the short circuit current can be undertaken in an inherently known manner.

The invention claimed is:

1. A sensor element that determines a concentration of gas components in a gas mixture, particularly of the concentration of gas components in an exhaust gas of an internal combustion engine, the sensor element comprising:
   a pumping cell having a solid electrolyte, an outer pumping electrode exposed to the gas mixture by the way of a porous protective layer, and an inner pumping electrode;
   a reference electrode disposed on the solid electrolyte and exposed to a reference gas;
   a Nernst electrode that with the solid electrolyte and the reference electrode constitutes a concentration or Nernst cell;
   wherein the sensor element is configured to at least periodically tap and analyze a Nernst voltage between the outer pumping electrode and the Nernst electrode.

2. A sensor element according to claim 1, wherein the sensor element is configured to tap a second Nernst voltage between the reference electrode and the outer pumping electrode.

3. A sensor element according to claim 1, further comprising a medium for commutation between a switching unit, through which a pumping voltage as a function of a deviation of a voltage lying at the reference electrode is controlled by a set point, and by a measuring device to tap the Nernst voltage between the outer pumping electrode and the Nernst electrode.

4. A method of operating a sensor element for a determination of a concentration of gas components in a gas mixture, particularly of a concentration of gas components in an exhaust gas of an internal combustion engines, the sensor element including a pumping cell having a solid electrolyte, an outer pumping electrode exposed to the gas mixture by way of a porous protective layer, and an inner pumping electrode; a reference electrode disposed on the solid electrolyte and exposed to a reference gas; and a Nernst electrode that with the solid electrolyte and the reference electrode constitutes a concentration or Nernst cell, the method comprising tapping and analyzing a measuring voltage between the Nernst electrode and the outer pumping electrode.

5. A method according to claim 4, further comprising drawing a conclusion about viscosities of the gas components from a chronological progression of the measurement voltage.

6. A method according to claim 4, further comprising drawing a conclusion about an aging of a catalytic converter, from which the sensor element is disposed downstream from a chronological progression of the measurement voltage.

* * * * *

UNITED STATES PATENT AND TRADEMARK OFFICE
CERTIFICATE OF CORRECTION

PATENT NO. : 7,780,829 B2
APPLICATION NO. : 11/632833
DATED : August 24, 2010
INVENTOR(S) : Diehl et al.

It is certified that error appears in the above-identified patent and that said Letters Patent is hereby corrected as shown below:

Front page, (75) Inventors: "Scheffel, Erlangen (DE)" should read --Scheffel, Gerlingen (DE)--

Signed and Sealed this
Eighteenth Day of January, 2011

David J. Kappos
*Director of the United States Patent and Trademark Office*